(12) United States Patent
Takayama et al.

(10) Patent No.: US 9,244,057 B2
(45) Date of Patent: Jan. 26, 2016

(54) MULTIPHASE MICROARRAYS AND USES THEREOF

(75) Inventors: Shuichi Takayama, Ann Arbor, MI (US); Hossein Tavana, Ann Arbor, MI (US); Arlyne Simon, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 13/635,697

(22) PCT Filed: Mar. 18, 2011

(86) PCT No.: PCT/US2011/028941
§ 371 (c)(1),
(2), (4) Date: Nov. 27, 2012

(87) PCT Pub. No.: WO2011/116256
PCT Pub. Date: Sep. 22, 2011

(65) Prior Publication Data
US 2013/0065784 A1 Mar. 14, 2013

Related U.S. Application Data

(60) Provisional application No. 61/315,183, filed on Mar. 18, 2010.

(51) Int. Cl.
| | |
|---|---|
| *C40B 40/14* | (2006.01) |
| *C40B 40/06* | (2006.01) |
| *C40B 50/14* | (2006.01) |
| *C40B 30/04* | (2006.01) |
| *G01N 33/50* | (2006.01) |
| *G01N 33/543* | (2006.01) |

(52) U.S. Cl.
CPC ........ *G01N 33/5008* (2013.01); *G01N 33/5436* (2013.01)

(58) Field of Classification Search
CPC ........ C40B 40/14; C40B 40/06; C40B 30/04; C40B 50/06
USPC .......................................... 506/9, 20, 18, 16
See application file for complete search history.

(56) References Cited

U.S. PATENT DOCUMENTS

| | | |
|---|---|---|
| 7,060,669 B1 | 6/2006 | Penttila et al. |
| 7,172,905 B2 | 2/2007 | Mrksich et al. |
| 2003/0185261 A1 | 8/2003 | Fisher et al. |
| 2005/0175501 A1 | 8/2005 | Thompson et al. |
| 2006/0078908 A1 | 4/2006 | Pitner et al. |
| 2008/0182240 A1* | 7/2008 | Anderson et al. .......... 435/6 |
| 2009/0209735 A1 | 8/2009 | Koo et al. |

FOREIGN PATENT DOCUMENTS

| | | |
|---|---|---|
| KR | 10-2007-0031759 A | 3/2007 |
| WO | 2010027590 A2 | 3/2010 |
| WO | WO 2010027590 A2 * | 3/2010 |

OTHER PUBLICATIONS

Hatti-Kaul, R., Aqueous Two-Phase Systems, Molecular Biotechnology, 2001, 19, 269-277.*
Takayama et al., "Teaching old liquids new tricks: Aqueous two-phase systems for cell and reagent micropatterning." Abstracts of Papers American Chemical Society 2009, 237: 336.
Greson, 1980, "Cell surface energy, contact angles and phase partition. I. Lymphocytic cell lines in biphasic aqueous mixtures", Biochimica Biophysica Acta, 602: 269-280.
Toshiyuki et al., "Micropatterning bacterial suspensions using aqueous two phase systems." The Analyst Jan. 1 2010, 135(11):2848.
Merchuk JC et al., "Aqueous two-phase systems for protein separation. Studies on phase inversion." J Chromatogr B Biomed Sci Appl. Jun. 26, 1998; 711(1-2):285-93.
Bamberger et al., "The partition of sodium phosphate and sodium chloride in aqueous dextran poly(ethylene glycol) two-phase systems." Journal of Colloid and Interface Science May 1984, 99(1):187-193.
Tavana H. et al., "Polymeric aqueous biphasic systems for non-contact cell printing on cells: engineering heterocellular embryonic stem cell niches." Adv. Mater. Jun. 25, 2010; 22(24):2628-31.
Rumiana Dimova: "Morphologies of Vesicles Loaded with Aqueous Polymer Solution." Zweijahresbericht Jul. 2008, Jun. 1, 2009, pp. 120-121.
Max Plannck Institute of Colloids and Interfaces, Report 2007-2008, Jun. 1, 2009, pp. 1-31.

* cited by examiner

*Primary Examiner* — Heather Calamita
*Assistant Examiner* — Amy M Bunker
(74) *Attorney, Agent, or Firm* — Casimir Jones SC

(57) ABSTRACT

The present invention relates to solution microarrays. In particular, the present invention relates to an aqueous 2-phase system for solution microarrays and uses thereof. Additional embodiments are described herein.

10 Claims, 10 Drawing Sheets

(a) Dry DEX film (b) Add PEG-cells ↓

(c) Incubate 30min ↓

(d) Add regular culture media ↓

(e) Monitor cell migration ↓

MULTIPHASE MICROARRAYS AND USES THEREOF

STATEMENT REGARDING FEDERALLY SPONSORED RESEARCH OR DEVELOPMENT

This invention was made with government support under HL084370 awarded by the National Institutes of Health. The government has certain rights in the invention.

CROSS REFERENCE TO RELATED APPLICATIONS

The present application is a national phase application under 35 U.S.C. §371 of PCT International Application No. PCT/US2011/028941, filed on Mar. 18, 2011, which claims priority to U.S. Provisional Patent Application Ser. No. 61/315,183 filed Mar. 18, 2010, each of which are herein incorporated by reference in its entirety.

FIELD OF THE INVENTION

The present invention relates to dehydrated solution microarrays. In particular, the present invention relates to arrayed multiphase assay systems and uses thereof.

BACKGROUND OF THE INVENTION

The identification of the entire genome sequences of many species, including humans, has set the stage for rapid advancements in the field of functional genomics. Information generated from functional analysis of genes will, in the long run, have major benefits for the prevention, diagnosis and management of many diseases which have been difficult to control. Given the large volume of data from the genome of complex organisms, functional genetic studies demand high-throughput methods to rapidly elucidate the function of many genes in parallel. Cell-based microarray systems are simple and low-cost, yet powerful tools that allow large-scale manipulation of genes in cells and analysis of corresponding downstream phenotypes. Currently, these arrays are realized by using either microwell plates that spatially segregate reagents using physical walls or solid substrates (glass or polystyrene) "printed" in certain spots with reagents suspended in a gel material. The printing method, also known as reverse transfection, offers higher density and simplified fluid handling once the reagents are printed and several groups have shown its potential for high-throughput studies of gene function. Nevertheless, this technique is inflexible in timing of delivery and removal of reagents, which limits the possibility of exposure of cells to a biochemical for a desired time period, and addition of certain components is required to stabilize transfection reagents. Most importantly, the printed gel that immobilizes reagents on the surface, by necessity, becomes the substrate to which cells attach and grow. This is a major concern for phenotypic assays since the influence of interactions between cells and their ECM on gene expression patterns of cells is ignored.

New methods are needed for cellular arrays to allow for parallel analysis of multiple genes in one assay.

SUMMARY OF THE INVENTION

The present invention relates to dehydrated solution microarrays. In particular, the present invention relates to arrayed multiphase assay systems and uses thereof.

For example, in some embodiments, the present invention provides a system, comprising: a) a first polymer solution (e.g., comprising a first polymer); b) a second polymer solution (e.g., comprising a second polymer), wherein the second solution is more dense that the first solution, and wherein the first and second solutions form an aqueous two-phase system when mixed, and wherein at least one of the first and second polymer solutions are dehydrated; and c) a solid or semi-solid support. In some embodiments, the first polymer solution is dehydrated, while in others the second polymer solution is dehydrated, and in further embodiments, both the first and second polymer solutions are dehydrated. In some embodiments, just the dehydrated polymer(s) are affixed to the support. In some embodiments, the polymer in solution (e.g., not dehydrated) is mixed with the dehydrated polymer solution to rehydrate the dehydrated polymer solution and form the 2-phase solution. In some embodiments, the first and second polymer solutions are rehydrated by an aqueous solution. In some embodiments, the system further comprises reagents for performing an assay (e.g., an immunoassay or a nucleic acid detection assay). In some embodiments, reagents for performing the assay are delivered in one or more of the hydrated polymer solutions, the dehydrated polymer solution, or an aqueous solution used to rehydrate polymer(s). In some embodiments, the aqueous solution comprises cells. In some embodiments, the first polymer is polyethylene glycol and the second polymer is dextran. In some embodiments, the first or second solutions comprise two or more polymers (e.g., DEX-methylcellulose, DEX-polyvinyl alcohol, PEG-DEX sulfate, polyvinyl alcohol-DEX sulfate, hydroxypropyldextran-DEX, or DEX sulfate-methylcellulose).

In further embodiments, the present invention provides a method, comprising a) contacting a solid or semi-solid support with a first solution comprising a first polymer (e.g., a dehydrated polymer) to form an arrayed support; b) contacting a portion of the arrayed support with a second solution comprising a second polymer (e.g., a dehydrated or hydrated polymer solution) wherein the first and second solutions form an aqueous two-phase system when mixed. In some embodiments, the first polymer solution is dehydrated, while in others the second polymer solution is dehydrated, and in further embodiments, both the first and second polymer solutions are dehydrated. In some embodiments, just the dehydrated polymer solution(s) are affixed to the support. In some embodiments, the support is for example, plastics, metal, glass, paper, fabric, hydrogels, foam, surfaces of sensors, electrodes, cantilevers, microfluidic device surfaces, inside capillaries, on medical devices, etc. In some embodiments, the polymer in solution (e.g., not dehydrated) is mixed with the dehydrated polymer solution to rehydrate the dehydrated polymer solution and form the 2-phase solution. In some embodiments, the first and second polymers are rehydrated by an aqueous solution. In some embodiments, the method further comprises delivering reagents for performing an assay (e.g., an immunoassay or a nucleic acid detection assay). In some embodiments, reagents for performing the assay are delivered in one or more of the hydrated polymer solution, the dehydrated polymer, or an aqueous solution used to rehydrate polymer(s). In some embodiments, one phase of the ATPS is dehydrated and the other is in solution. In other embodiments, multiple phases are dehydrated together. In some embodiments, the aqueous solution comprises cells. In some embodiments, the first polymer is polyethylene glycol and the second polymer is dextran. In some embodiments, the first or second solutions comprise two or more polymers (e.g., DEX-methylcellulose, DEX-polyvinyl alcohol, PEG-DEX sulfate, polyvinyl alcohol-DEX sulfate, hydroxypropyldextran- DEX, or DEX sulfate-methylcellulose). In some embodiments, the dehydrated polymers are lyophilized or dried. In some embodiments, the aqueous solution is a bodily fluid (e.g., blood, urine, saliva or serum). In some embodiments, the aqueous solution comprises cells. In some embodiments, the cells are excluded from at least a portion of the aqueous two phase solution. In some embodiments, the cells form patterns in multi well plates (e.g., exclusion zones). In some embodiments, the cells are used in an assay (e.g., a cell migration assay).

Additional embodiments of the present invention provide a method, comprising a) arraying a plurality of first solutions comprising i) a first polymer; and ii) reagents for performing an immunoassay on a solid or semi-solid support; b) dehydrating the solution to form dehydrated spots on the support; c) contacting the dehydrated spots with a second solution comprising a second polymer and a test sample under conditions such that the second solution rehydrates the dehydrated spots and forms an aqueous two phase solution. In some embodiments, the method further comprises the step of identifying the presence of one or more antigens in the test sample. In some embodiments, the plurality of first solutions each comprise an antibody specific for a different antigen.

Additional embodiments are described herein.

DEFINITIONS

Figure 1:
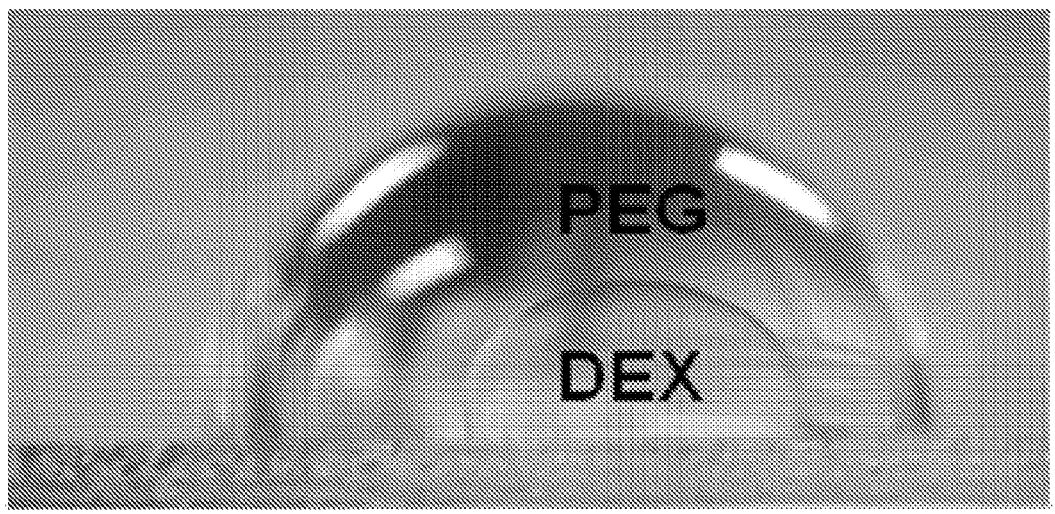
FIG. 1 shows a side view image of rehydrated DEX droplet (0.3 µL) after exposure to PEG (6.0 µL).

To facilitate an understanding of the present invention, a number of terms and phrases are defined below:

The term "sample" in the present specification and claims is used in its broadest sense. On the one hand it is meant to include a specimen or culture. On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

As used herein, the term "cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk-cell lines, the CAD gene that is used in conjunction with CAD-deficient cells and the mammalian hypoxanthine-guanine phosphoribosyl transferase (hprt) gene that is used in conjunction with hprt-cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present invention. In some embodiments of the present invention, test compounds include antisense, siRNA or shRNA compounds.

DETAILED DESCRIPTION OF THE INVENTION

The present invention relates to solution microarrays. In particular, the present invention relates to an aqueous 2-phase system for solution microarrays and uses thereof. In some embodiments, the present invention provides compositions and methods for addressing cells and reagents to one of the multiple phases of an aqueous multi phase cell culture system. In some embodiments, the system and methods are used to deliver reagents (e.g., nucleic acids in a transfection complex or viruses) to arrays of cells. The solution based arrays allow for precise and accurate delivery of reagents to only those locations desired and not to others. Although the compositions and methods described herein are illustrated with the use of printing on cells, the present invention is not limited to printing on cells. The "cell" surface may be replaced by surfaces other than cells and work in a similar manner. In some embodiments, the aqueous 2-phase system is dehydrated on the microarray, providing additional stability and functionality.

I. Microarrays

In some embodiments, the present invention provides multi (e.g., 2) phase solution based microarrays. The present invention is not limited to particular components of the microarray. In some embodiments, microarray comprise aqueous polymers. Preferred polymers are those that form an aqueous two phase system (ATPS) at a wide range of temperatures (See e.g., WO 2010/027590; herein incorporated by reference in its entirety). Any system that selectively partitions larger molecules (e.g., cells) or smaller molecules (e.g., nucleic acids or viruses) may be utilized. Examples of suitable polymers include, but are not limited to, polyethylene glycol (PEG), dextran (DEX), and combinations of other polymers such as DEX-methylcellulose, DEX-polyvinyl alcohol, PEG-DEX sulfate, polyvinyl alcohol-DEX sulfate, hydroxypropyldextran-DEX, and DEX sulfate-methylcellulose.

In other embodiments, ATPS that exhibit variable phase separation with temperature are utilized. In some embodiments, such systems utilize low molecular weight polymers.

In some embodiments, the first layer (e.g., PEG containing media) is dispensed onto cells (e.g., a confluent layer of cultured cells). In some embodiments, genetic material to be transferred to the array is placed in the wells of a multi well (e.g., 1536 well) plate. In some embodiments, the molecule of interest (e.g., genetic material) is in a solution containing the second component of the ATPS (e.g., Dex). In some embodiments, a transport component (e.g., an array of slot pins) is then used to transfer the molecule of interest onto the cell array. For example, in some embodiments, a multiplex dispenser that allows different materials to be added to different spots on the array is utilized. In some embodiments, the dispenser is a plurality of pins or other dispensing components affixed to a single transport component. In some embodiments, the transport component is automated.

In some embodiments, the component comprising the molecule of interest is denser that the first component and thus displaces the first material and contacts the cells. In some embodiments, cells are then transfected with the genetic material.

II. Dehydrated ATPS

Embodiments of the present invention provide ATPS that comprise one or more dehydrated components. Experiments conducted during the course of development of embodiments of the present invention describe a facile, reliable, and scalable method to spatially pattern, dry, and rehydrate droplets of two incompatible aqueous polymer solutions.

A variety of multiplexed assays have been reported in the literature and a number of systems have even been commercialized (Luminex, Mesoscale, Aushon, etc). These multiplexed assays, however, have not been adapted successfully to clinical settings, even in well-equipped hospitals of developed countries. The primary reason is the multiplicity of challenges associated with assay validation. One limitation of existing sandwich assays (so-called ELISA and related sandwich immunoassays that are required for clinically appropriate specific and sensitive detection of many important biomarkers) is that although the primary antibody can be arrayed separately, the secondary antibody is introduced as a cocktail. The difficulty of validation increases exponentially as the number of assays to be multiplexed increases. If any one of the reagents or antibody becomes defective, the entire assay is jeopardized. This reduces reliability of the entire assay. Any replacement of reagents, even with extreme attention to the integrity of the reagents, requires revalidation of the entire combination and a separate "standard curve". This greatly reduces versatility and increases cost. What is needed to enable efficient and robust point-of-care diagnoses, therefore, is improved multiplexed biomarker analysis technology where sandwich immunoassays can be efficiently multiplexed without "reagent crosstalk" problems.

In some embodiments, the present invention provides dehydrated aqueous multi (e.g., two) phase systems. In some embodiments, one phase of the system is dehydrated. In some embodiments, the system is rehydrated with a solution of the other phase to reconstitute the aqueous two phase system.

In some embodiments, all phases of an aqueous two phase system are dehydrated. In such embodiments, the system may be rehydrated using any number of suitable solutions. Examples include, but are not limited to, water or aqueous solution that does not include either of the components of the aqueous two phase system, samples (e.g., blood, urine, serum, semen, saliva or components thereof, etc.

The present invention is not limited to a particular method of dehydrating ATPS components. Examples include, but are not limited to drying or lyophilization.

In some embodiments, the dehydrated phase(s) is patterned or arrayed on a solid surface. In some embodiments, the support or solid surface is for example, plastics, metal, glass, paper, fabric, hydrogels, foam, surfaces of sensors, electrodes, cantilevers, microfluidic device surfaces, inside capillaries, on medical devices, etc.

In some embodiments, dehydrated phase(s) comprise reagents that partition selectively to that phase and remain in that phase when rehydrated. In some embodiments, the reagent is an immunoassay reagent such as bead proximity assay reagents. In some embodiments, the reagent is a nucleic acid reagent for transfection, gene knockdown, or molecular beacon type detection assay reagent.

In some embodiments, the rehydrating solution contains cells. In some embodiments, cells in the rehydrating solution are excluded from the pre-patterned aqueous two phase system to form patterns of cell attachment (e.g., on a solid support such as a multi-well plate). In some embodiments, the patterned cells are used for assays (e.g., cell migration assays or migration inhibitor assays).

Additional uses for dehydrated ATPS are described herein.

III. Uses

The solution based microarrays of the present invention find use in a variety of applications. Any application that requires manipulation of cells, reagents or surfaces in an array format is amenable to the methods of the present invention.

In some embodiments, the compositions and methods of the present invention find use in transfection methods. For example, in some embodiments, cells to be transfected are placed under the first solution. The genetic material is placed in the second solution and selectively delivered to cells. The present invention is not limited to a particular type of genetic material. Examples include, but are not limited to, DNA, virus, phage, RNA (e.g., antisense, shRNA or siRNA) or DNA encoding antisense, shRNA or siRNAs. Using such methods, it is possible to deliver multiple different types of genetic material to the same array of cells.

In some embodiments, cells are transfected using ultrasound. For example, in some embodiments, DNA is delivered to specific cells using the ATPS systems described herein and ultrasound contrast agent bubbles are used to introduce genetic material into cells via ultrasound.

In other embodiments, additional transfection systems and reagents are included (e.g., lipid based transfection systems, electroporation systems, etc.).

In some embodiments, the compositions and methods of embodiments of the present invention are used in cell migration assays. In some embodiments, the migration assay is based on movement of cells from a confluent monolayer into a circular cell-excluded area within the monolayer. In some embodiments, an aqueous two-phase system is utilized to create cell-exclusion patterning (See e.g., Example 4). In some embodiments, cell-exclusion patterning is used in cell migration (e.g., drug screening and research applications). For example, in some embodiments, cells are treated with test compounds and their migration is assayed.

In other embodiments, the compositions and methods of the present invention find use in drug screening applications. For example, in some embodiments, cells to be screened (e.g., cancer or disease cells) are placed under the first solution. Candidate compounds are then placed in the second solution and selectively delivered to cells. In some embodiments, candidate compounds are therapeutic nucleic acids (e.g., siRNA, antisense or DNA encoding therapeutic RNAs). Using such methods, it is possible to deliver multiple different candidate compounds to the same array of cells.

In other embodiments, cells are contacted with additional molecules of interest including, but not limited to, cell signaling molecules (e.g., cytokines), growth factors, proteins, etc. and the effect of the molecule on the cell is assayed.

In still further embodiments, the present invention provides systems and methods for detecting cell-cell and cell-tissue interactions. For example, in some embodiments, a substrate immersed in a first solution is printed with cells suspended in a second solution, allowing localized delivery. The cellular array can then be contacted with a second cell or cell type (e.g., to study cell-cell interactions) or a tissue (e.g., for use in tissue engineering or research).

Following manipulation of cells, altered (e.g., transfected) cells may be detected using any suitable read out method. In some embodiments, the read out is an immunofluorescence method where antibodies to protein expressed from a transfected cell is contacted with the transfected array. Fluorescence is detected using any suitable method (e.g., a microscope or a fluorimeter).

In other embodiments, a different detection method including, but not limited to, fluorescence in situ hybridization, reporter assay (e.g., with fluorescence, chemical or chemiluminescence readout) or other detection method is utilized.

In some embodiments, cell based array methods and read out is performed in a high throughput manner. In some embodiments, high throughput methods are automated.

In some embodiments, the present invention provides compositions and methods for assaying cell migration. Cell migration is a fundamental process during events such as cancer metastasis and the failure of diabetic wound healing. Understanding molecular mechanisms responsible for dysregulated cell migration greatly benefits from high throughput technologies that allow screening libraries of small molecules or siRNAs to identify potential therapeutic compounds. To date, the majority of in vitro cell migration studies rely on the conventional wound healing and Boyden chamber assays. These approached are limited in throughput and implementation in formats smaller than 96-well plates. An Oris cell migration assay has also been developed that utilizes a physical barrier resting on the surface to generate individual islands of naked surface surrounded by a cell monolayer in wells of a 96 well plate. Migration of cells into the empty space is studied after removal of the barrier. The technique is cumbersome due to the use of various components the need for several wash and incubation steps. More importantly, the physical contact of the barrier with the surface can be damaging to underlying soft extracellular matrix hydrogels. Therefore, new approaches that enable cell migration studies in higher throughputs are required.

Accordingly, in some embodiments, the present invention provides compositions and methods for assaying cell migration. In some embodiments, the assays utilize ATPS comprising one or more dehydrated components.

In some embodiments, the compositions and methods of embodiments of the present invention find use in immunoassays. In some embodiments, the present invention provides multiplexed immunoassays where the sample solution is simultaneously exposed to multiple analyte assay droplets where the primary and secondary antibody reagents for each analyte are segregated into the different droplets with no crosstalk of reagents between the assay droplets. In some embodiments, aqueous two phase systems where immunoassay reagents (both primary and secondary antibodies) are localized into microarrayed dehydrated droplets of one aqueous phase and subsequently the droplets are exposed to sample contained in the second aqueous phase are used. The aqueous two phase system and reagents are designed to allow biomarkers to diffuse from the sample-containing aqueous phase into the assay droplet phase, but the immunoassay reagents does not diffuse out of the assay droplets. These solution microarray assays enable flexible adaptation to analyze different panels of biomarkers such as, for example, antigens, antibodies, cytokines, interleukins, drugs, etc. to diagnose pathogens, infection, inflammation, compliance, and other point-of-care needs.

An example of immunoassays that can be performed within, for example, dehydrated ATPS droplets include, but are not limited to, proximity bead based assay reagents (e.g. AlphaLISA, PerkinElmer) pre-arrayed and dried in a microarray format with first and second polymers (e.g., dextran (DEX) and polyethylene glycol (PEG)). Body fluid sample is wicked over the dehydrated array of individual immunoassays. In one step, the body fluid sample is exposed to all the arrayed spots where each droplet has immunoassays for different biomarkers. Each spot becomes hydrated and forms distinct phase-separated droplets. Engineered sandwich immunoassay reagent beads against various biomarkers stably partition within each first polymer phase and do not diffuse out into the second polymer phase. Thus, there is no cross-talk of antibodies between different assay droplets. On the other hand, immune system biomarkers (proteins) diffuse freely from one phase to another allowing interaction with the immunoassay reagent beads confined within each phase droplet. Once the biomarker brings the primary antibody-bead and secondary antibody-bead into close proximity, a chemiluminescent or other signal is produced. This bead proximity assay requires no washing or other fluidic manipulation. The simplicity of procedures plus the ability to self-contain each sandwich immunoassay in separate solution droplets with no cross-talk between antibodies, gives the technology reliability, flexibility, and scalability.

In some embodiments, the reagent in the first polymer is a molecular beacon or other nucleic acid detection reagent and multiplexed DNA detection is performed. In other embodiments, the reagent is a proximity scintillation reagent or a fluorescent polarization immunoassay reagent. In some embodiments, the reagent storage stability is enhanced because dried forms are more stable than solutions and because sugars, including dextran, often enhance stability of dehydrated forms of reagents.

The present invention further provides systems and kits comprising the solution arrays described herein. In some embodiments, systems and kits comprise cells (e.g., in a multiwell solid support), multiple solutions for forming arrays, transport components (e.g., robotics), and components for read out of signal from altered cells, including analysis software. In some embodiments, kits further comprise additional component useful, necessary, or sufficient for performing and analyzing the results of the methods described herein (e.g., including, but not limited to, buffers, nucleic acids, candidate drug compounds, etc.).

EXPERIMENTAL

The following examples are provided in order to demonstrate and further illustrate certain preferred embodiments and aspects of the present invention and are not to be construed as limiting the scope thereof.

Example 1

Dehydrated Aqueous Polymer Solutions

This example described a method to spatially pattern, dry, and rehydrate droplets of two incompatible aqueous polymer solutions. A polymeric aqueous two phase system (ATPS) with 2.5% (w/w) poly(ethylene glycol) 35,000 (PEG) and 3.2% (w/w) or higher dextran 500 (DEX) as the phase forming polymers were used. In the ATPS solution, PEG always forms the upper phase whereas DEX always forms the lower phase.

Aqueous solutions are hydrophilic; thus, when deposited onto hydrophilic substrates (e.g. glass), the solutions "spread" out over the surface and the contact angle measured is less than 90°. If deposited onto a hydrophobic surface, however, aqueous solutions bead onto the surface or exhibit poor wettability and the contact angle measured exceeds 90°. The contact angle quantifies the angle at which the solid substrate intersects the liquid droplet/vapor interface.

Rehydrating Dextran Droplets by Addition of Poly(Ethylene Glycol)

To generate a spatially patterned microarray of DEX droplets, 0.2 μL-1.0 μL DEX phase was dispensed onto poly (dimethylsiloxane) (PDMS), polystyrene, or glass substrates. DEX droplets were allowed to evaporate at room temperature and the length of time required for complete evaporation depends upon the initial droplet volume. After evaporation, dried discrete films of DEX remain adhered to the surface. Addition of an aqueous PEG solution to the dried DEX films causes the DEX droplets to rehydrate as illustrated in FIG. 1.

Rehydrating ATPS Droplets by Addition of Water

Figure 2:
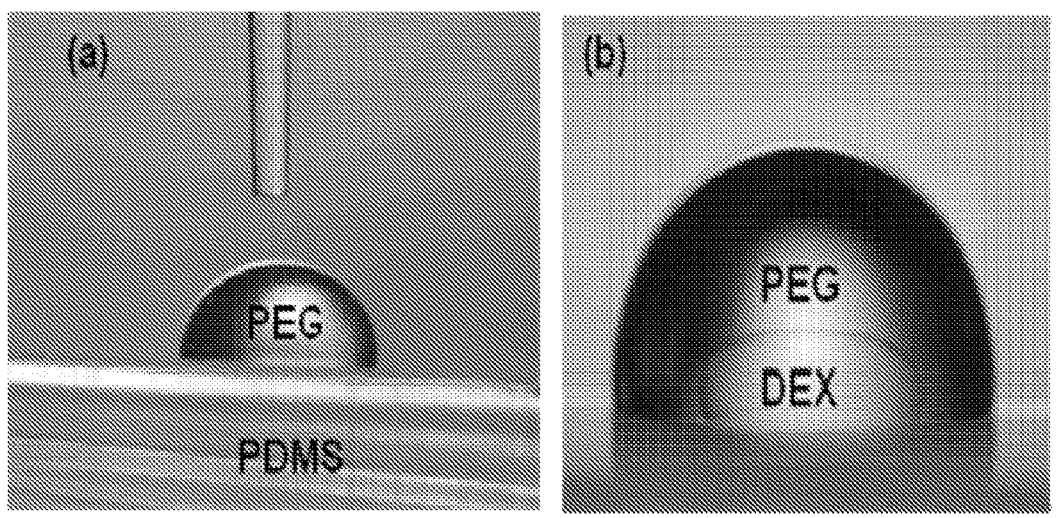
FIG. 2 shows (a) PEG (6.0 µL) is dispensed onto a PDMS substrate. DEX phase is introduced into the PEG solution using a dispensing tool. ATPS is allowed to evaporate. (b) Addition of water yields rehydration of DEX and PEG droplet and regeneration of ATPS.

To generate a discrete islands of ATPS droplets, first PEG solution is dispensed onto poly(dimethylsiloxane) (PDMS), polystyrene, or glass substrates. The appropriate DEX phase is subsequently introduced into the PEG phase using a dispensing tool (FIG. 2 (a)). After equilibration of the two immiscible aqueous polymer solutions, a distinct PEG-DEX interface is readily observed via an appropriate optical setup. The ATPS solution is allowed to evaporate at room temperature for a few minutes to several hours. Upon addition of water or some other aqueous solutions that do not contain significant amounts of either the PEG or DEX at room temperature, the PEG-DEX drop stably rehydrates to once again form an ATPS (FIG. 2(b)).

Example 2

Figure 3:
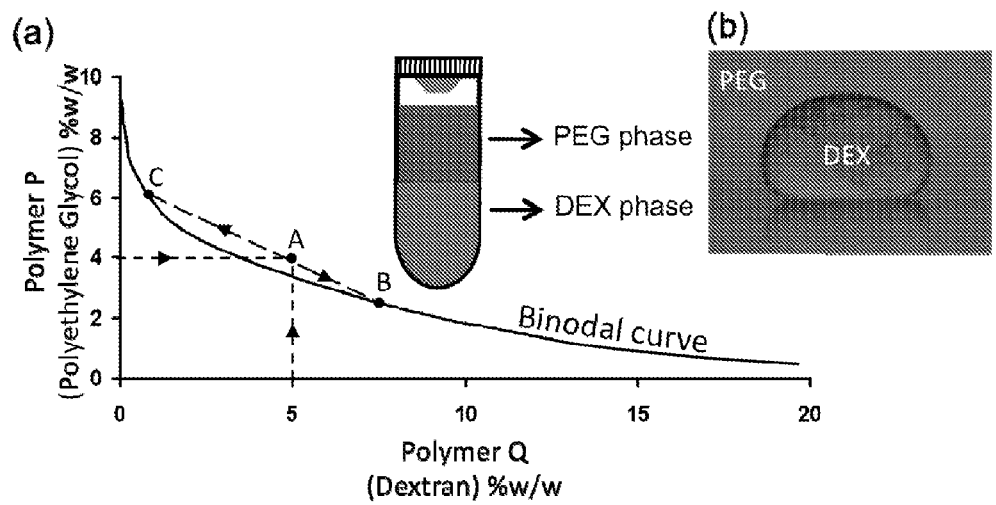
FIG. 3 shows (a) Phase diagram of an aqueous two-phase system (ATPS) with Polyethylene glycol (PEG) and Dextran (DEX) as phase forming polymers is shown. The diagram describes the composition of each phase and the range of concentrations that results in phase separation. Only those combinations of the two polymers P (PEG) and Q (DEX) above the binodal curve give an ATPS. Point A represents a typical initial concentration of each polymer in the entire solution whereas points B and C describe the compositions of bottom and top phases in equilibrium, respectively. (b) Due to density difference between the two phases, a drop of the denser phase, DEX, can be formed within a bath of the less dense immersion phase, PEG.
Figure 4:
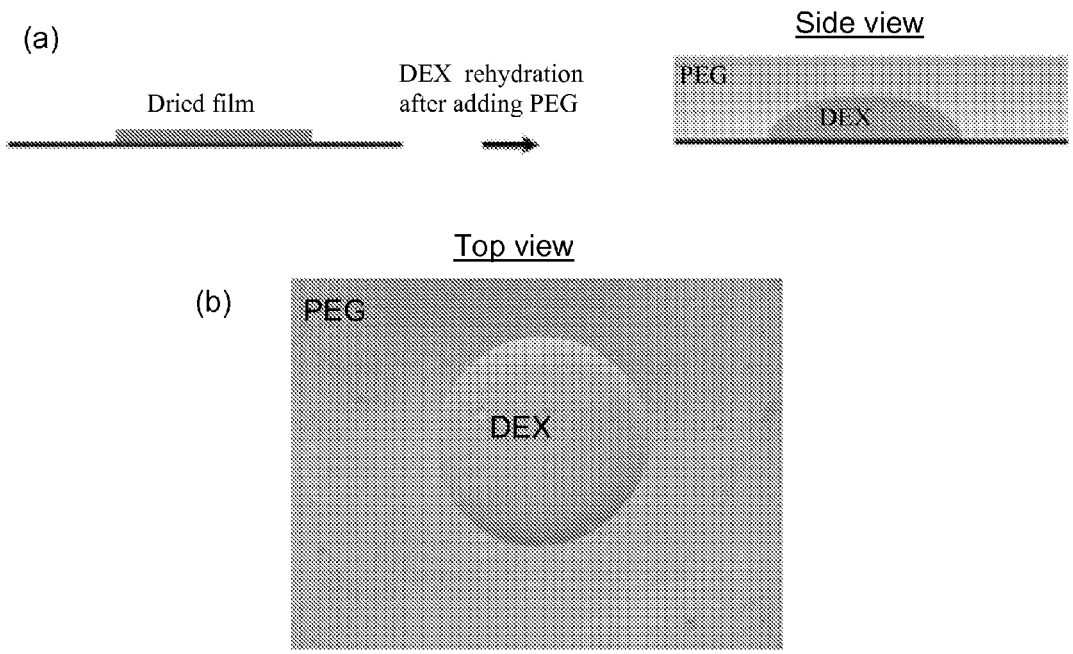
FIG. 4 shows (a) A drop of the denser phase, DEX, is dried in ambient air. Subsequent addition of the immersion phase, PEG, results in the rehydration of the dried DEX film and formation of a DEX drop. (b) Top view of an actual DEX droplet formed after rehydration with the immersion PEG phase.

This example describes a system that provides a cell migration assay in a high density format such as a 384 microplate format in a single step without the need for multiple washing and incubation steps. The system is based on the use of a cell culture compatible aqueous two-phase system (ATPS) consisting of polyethylene glycol (PEG) and Dextran (DEX) as the phase forming polymers (FIGS. 3-4) and based on the following principle. A nanoliter droplet of the DEX phase is printed on a cell culture dish and left in a sterile culture hood to allow the water content of the droplet to evaporate and leave a thin solid film of DEX on the surface. Addition of the aqueous PEG phase into the dish results in the rehydration of the dried DEX film and formation of a DEX droplet phase-separated from the surrounding PEG phase.

Figure 5:
FIG. 5 shows the procedure for creating cell-exclusion migration assay: (a) the DEX phase is dried to a thin film, (b) cell suspension is mixed with the PEG phase and gently added to the dish containing dried DEX film, (c) the DEX phase rehydrates to form a droplet and cells adhere only to the surface around the droplet during incubation, (d) regular culture media is added to dilute out the ATPS resulting in an empty space Where the DEX drop Was located, (e) cells migrate into the empty space.
Figure 5:
Figure 5:
Figure 5:
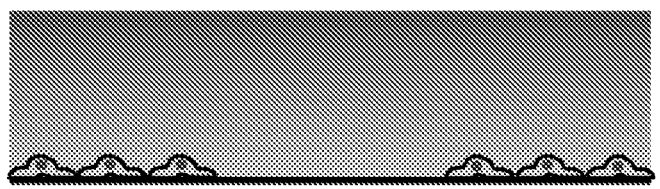
Figure 5:
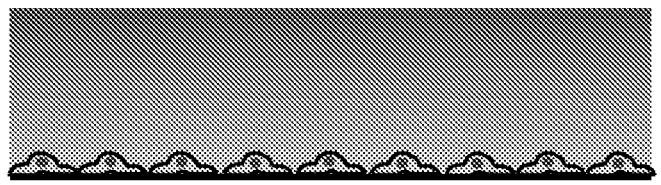

This method was used to generate a monolayer of cell surrounding a circular area defined by the size of the rehydrated DEX droplet. Suspension of cells is mixed with the PEG phase and added to the culture dish containing a DEX film. Cells mainly adhere to the surface around the rehydrated DEX drop and the interfacial tension between the PEG phase and the aqueous DEX phase prevents cells from penetrating into the droplet. After incubation for 30 min, culture medium is added to increase the volume to working volume. This dilutes out the polymer content of the culture system and results in a single aqueous phase. Migration of cells into the available empty space can then be monitored. FIG. 5 depicts this procedure. This system has been adapted to a high throughput 384 well plate format by using a robotic liquid handler to print a DEX droplet into each well of a 384 microplate and enable high content screening of cell migration.

Example 3

Figure 6:
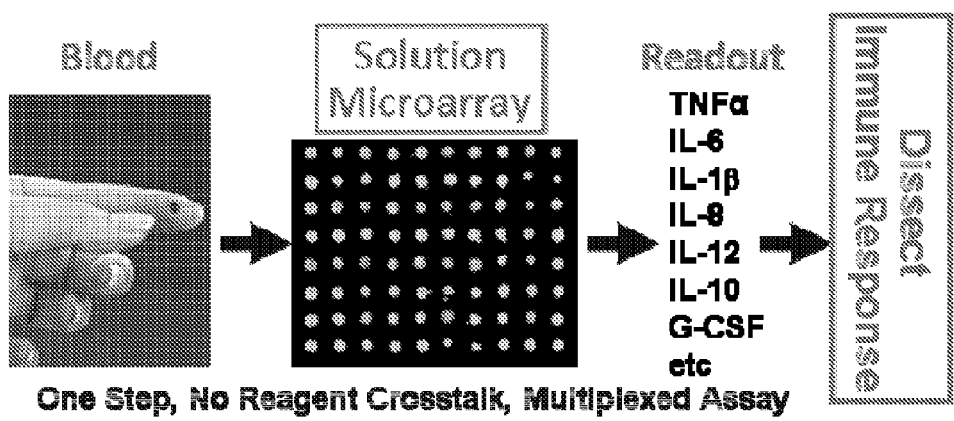
FIG. 6 shows small volumes of sample injected over an array of dehydrated nanoliter drops of aqueous two phase systems containing assay reagents. Multiplexed assays performed in one step with no crosstalk of reagents between different assay solution spots providing robust readouts.
Figure 7:
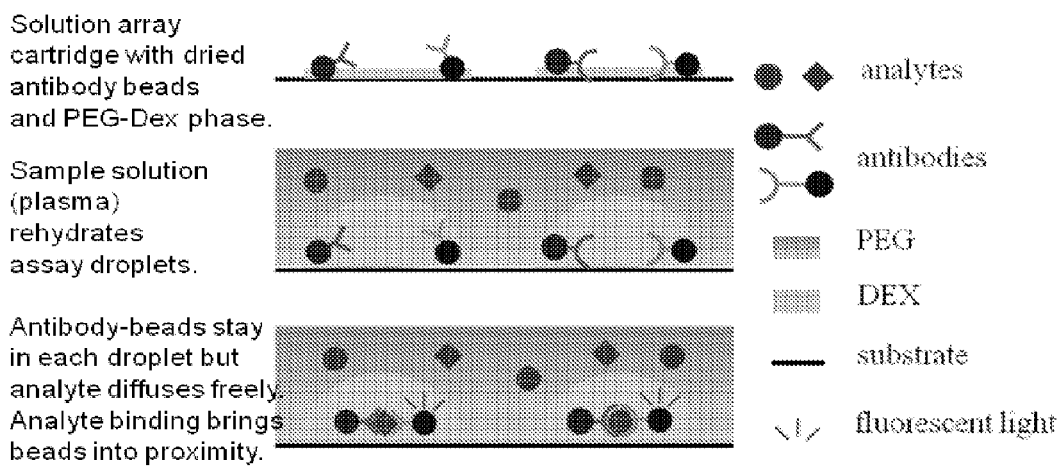
FIG. 7 shows a side view of the solution array assay. (top) Array of dried DEX and immunoassay reagent beads. (middle) Specimen solution rehydrates DEX droplets and PEG phase. (bottom) Analytes bind and light up droplets containing antibodies specific to particular analyte.

This Example describes an exemplary immunoassay system. FIGS. 6-7 illustrate an exemplary embodiment of the system. The following solution was incubated in a reaction tube for 1 hour: in DEX500-PBS (final 3.2% w/w), Anti-TNFα alpha acceptor beads (final 20 μg/mL), Biotinylated Antibody Anti-TNFα (final 3 nM), Streptavidin-Donor beads (final 40 μg/mL). In a 2nd tube, TNFα analyte (varied concentrations) in PEG35K-PBS (2.5% w/w final) was incubated for one hour. It was not necessary to incubate TNFα in PEG but it decreases prep time for mixing PEG and DEX phases for readings if samples are already prepared.

All reagents were prepared in a darkly lit room/Cell culture hood, wrapped in foil and placed in desk drawer for incubation period.

Figure 8:
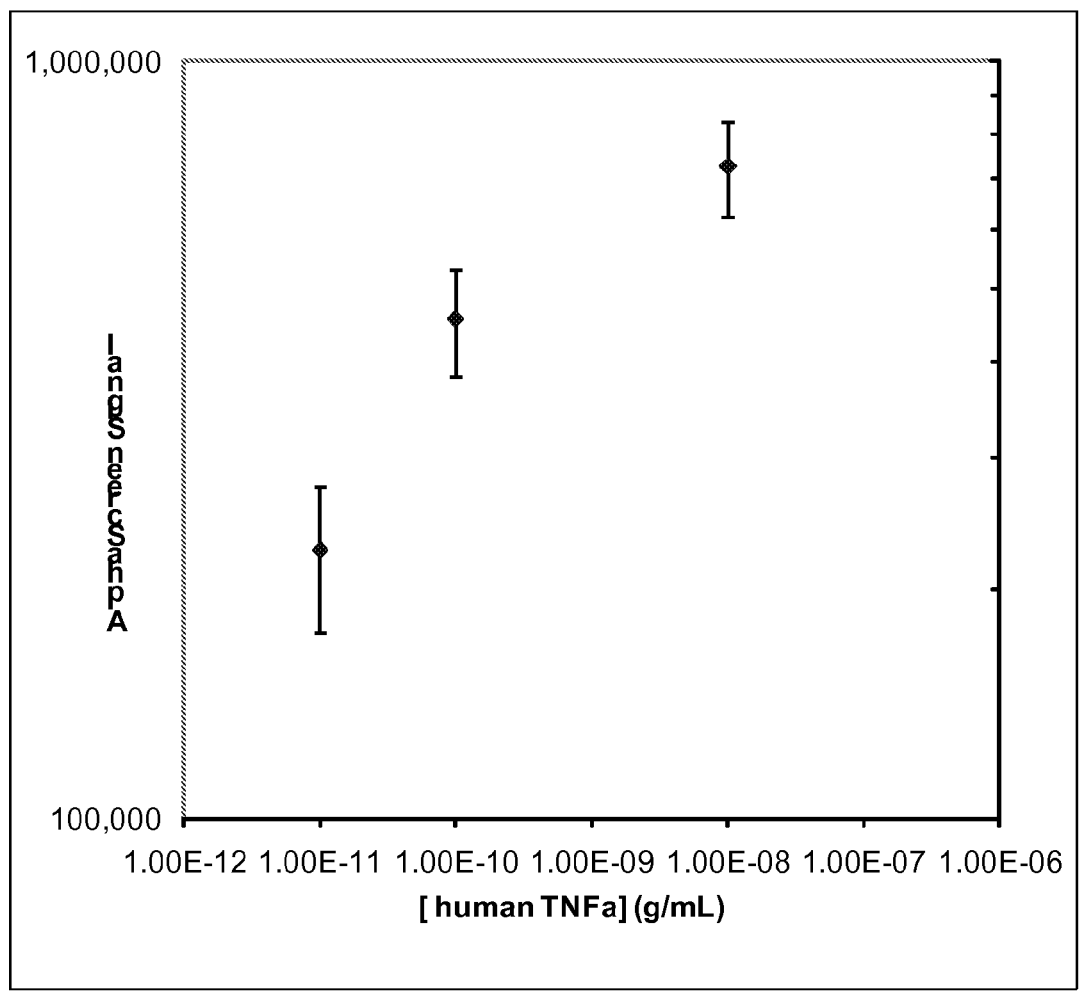
FIG. 8 shows results of performing alphalisa assay for TNFα using aqueous two phase systems.

Next, the ATPS mixture was pipeted into a well of an Opti-Plate 384. The microplate was placed into a PHERAStar Microplate reader for an hour to cause PEG and DEX to equilibrate and form two-phase system. The AlphaLISA signal is temperature sensitive the microplate was brought to temperature of plate reader. Readings are then taken. It was observed that readings could be taken well into the low pg/mL or femtomolar range of TNFα (FIG. 8).

This ATPS immunoassay microarray has advantages over conventional assays even if not performed with dehydrated ATPS in that the amounts of reagents used can be small, and multiple microscale singleplex assays can be performed in parallel without significant crosstalk of reagents as occurs in conventional multiplexed immunoassays.

Example 4

Experimental

Phase Diagram Formation

Stock solutions of 20% (w/w) PEG (Mw: 35,000, Fluka) and 20% (w/w) DEX (Mw: 500,000 Pharmacosmos) were prepared in $dH_2O$. In 10 ml conicals, 19 ATPSs of differing compositions ranging from 0.56% (w/w) PEG-19% (w/w) DEX to 16% (w/w) PEG-0.94% (w/w) DEX were prepared using the stock phase solutions. The weight of each conical with the ATPS was recorded. Each ATPS was titrated drop-wise with $dH_2O$ until a single phase was obtained. The conical was centrifuged at 2000 g for 3 min to ensure formation of a single phase. The final weight of the conical with the one-phase system was recorded and used to calculate the weight of diluent added for one-phase formation. The binodal was determined through plotting the final composition of each system. A relationship derived by Merchuk et. al was fitted to the data using a non-linear least squares regression (Merchuk et al., *J. Chromat. B* 1998, 711, 285).

Printing of Cell-Excluding DEX Droplets in 96-Well Plates 6.4% (w/w) solution of the DEX 500K phase was prepared in culture media and kept at 4° C. until use. The tip magazine of an automated liquid handler (CyBi-Well, CyBio) was loaded with 96 sterile 25 μl pipette tips (CyBio). 75 μl of the DEX solution was pipetted into each well of a 96-well microplate (Corning), which was then placed on the stage of the liquid handler. To load pipette tips with the DEX solution, the stage was slowly raised until the pipette tips were slightly inside the DEX solution. 10 μl of the DEX solution was aspirated into the tips at a rate of 5 μl/s. The loaded tips were brought within 200 μm of the bottom of the wells of an empty microplate and 0.8 μl of the DEX solution was dispensed onto the surface at a rate of 0.5 μl/s to form circular droplets. The microplate was kept in a culture hood for at least 24 hrs to allow the droplets to dry. Images of the dried droplets were captured using a bright-field microscope (Nikon, TS-200). The Feret diameters of the droplets were determined using the "Analyze Particles" function of ImageJ (NIH). Droplets whose Feret diameters were not within ~1% of the desired mean diameter were excluded from use in the assay. The entire printing and drying process was performed in a sterile culture hood.

Cell Culture

Three different human cancer cell lines were used: MDA-MB-231 breast cancer cells (ATCC) were cultured in DMEM medium supplemented with 10% heat-inactivated fetal bovine serum (HI-FBS, Invitrogen), 1% glutamine (Invitrogen), and 1% antibiotic. A549 lung cancer cells (ATCC) were cultured using F-12K medium (ATCC) supplemented with 10% HI-FBS and 1% antibiotic. PC-3 prostate cancer cells were maintained in DMEM supplemented with 10% HI-FBS and 1% antibiotic. Cells were maintained in a cell culture incubator at 37° C. with 5% $CO_2$ and 95% humidity. When at desired confluence, cells were washed with PBS and Hank's-based enzyme-free cell dissociation buffer was added to the flask. Cells were incubated for 30 min and then collected and suspended in complete growth medium. After centrifuging down for 5 min at 4° C. and 1000 rpm, cells were resuspended in appropriate volume of the culture medium to give a density of $2 \times 10^6$ cells/ml.

Cell-Exclusion Patterning Using the Two-Phase Media 5.0% (w/w) solution of the PEG 35K phase was prepared in culture media and kept at 4° C. until use. This solution was added to the cell suspension at a 1:1 (v/v) ratio to give a final PEG phase concentration of 2.5%. Prior to this step, cell suspension density was adjusted by addition of culture media to result in a final density of $4.5 \times 10^4$ MDA-MB-231 cells, $4.0 \times 10^4$ A549 cells, and $4.5 \times 10^4$ PC-3 cells after addition of the PEG-containing media. These cell densities were selected from preliminary experiments that evaluated the number of cells required to form a confluent monolayer per unit surface area. 80 μl of the resulting solution was added to each well of a 96-well plate, which was incubated at 37° C. with 5% $CO_2$ and 95% humidity overnight (12 hrs). Then, the two-phase media was washed out and replaced with regular culture media. This was set as the time zero of the migration experiment.

Treatment of Cells with Blebbistatin and Anti-Cancer Drugs

After allowing MDA-MB-231 cells to spread and form a confluent monolayer around the cell excluded gaps, they were treated with (±)-blebbistatin at different concentrations in the range 5-200 μM or anti-cancer drugs paclitaxel, colchicine, and nocodazole in the concentration range of 1-1000 nM. Cells were incubated for 18 hrs in the presence of blebbistatin, washed with PBS once, and regular culture medium was added. Incubation continued for another 12 hrs before imaging. To study the effect of anti-cancer drugs, cells were incubated with each drug for 2 hrs, washed with PBS, and then supplied with culture medium. Imaging was performed after 30 hrs of incubation. Experiments were set in 30 replicates. All reagents were purchased from Sigma.

Cellular Staining

After migration experiments were complete, cells were stained with a 5 μM Calcein AM and the plates were incubated at 37° C. for 30 min. The dye solution was gently removed and culture medium was added to wells.

MDA-MB-231 cells were stained for actin filaments. First, cells were fixed in a 4.0% paraformaldehyde (Sigma) solution for 10 min. After washing cells with PBS, they were permeabilized with 0.1% Triton X-100 (Sigma) solution in PBS for 5 min. To reduce nonspecific binding, cells were treated with 1.0% BSA as the blocking reagent for 30 min. Cells were incubated with Alexa Fluor 594-conjugated Phalloidin at a concentration of 165 nM for 20 min. Finally, cells were washed three times with PBS before imaging using an inverted fluorescence microscope (Nikon, TE300). The resulting images were pseudocolored in Photoshop 10.0 CS3 (Adobe).

Results

Principles of Cell-Exclusion Patterning and Cell Migration

Figure 9:
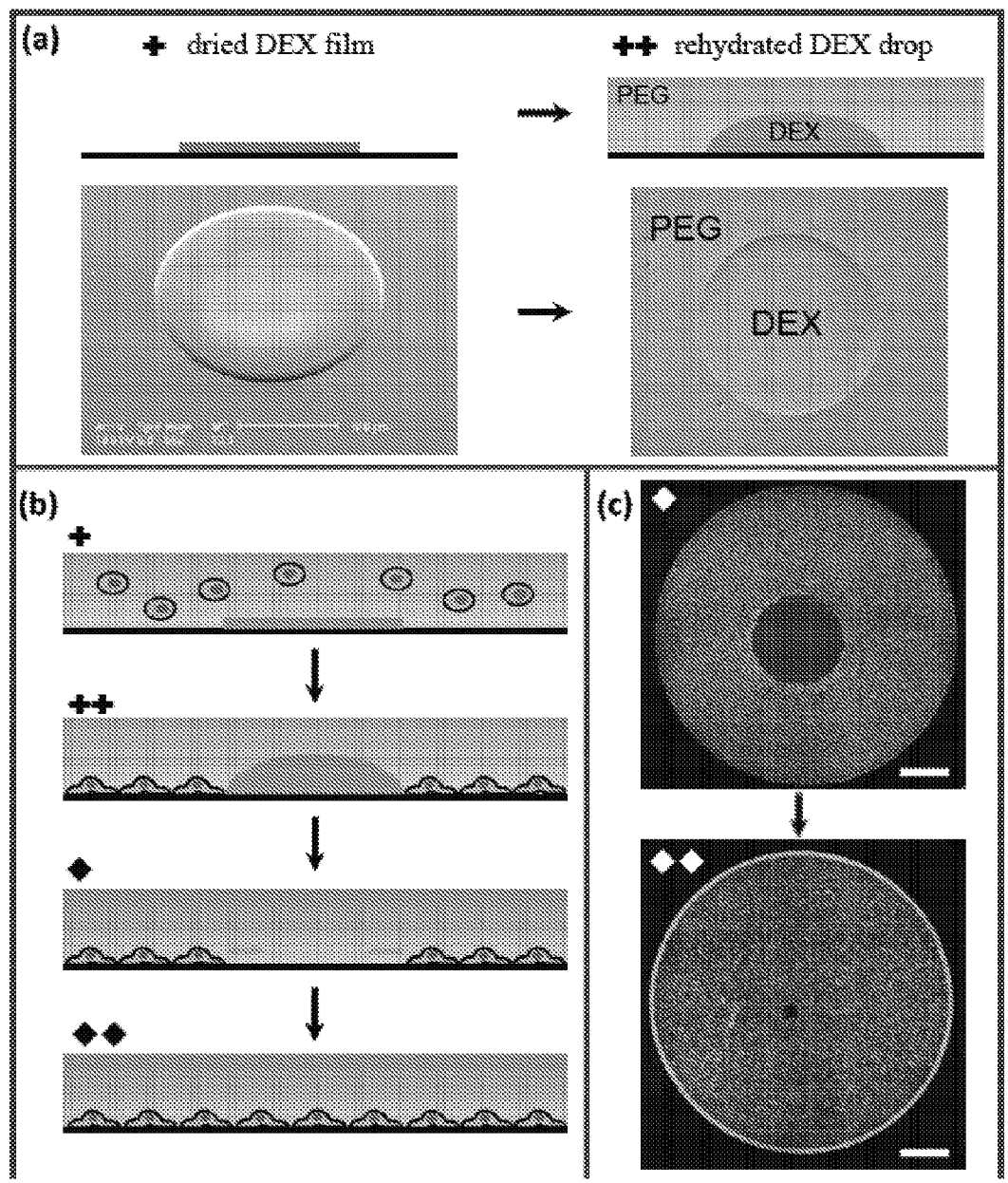
FIG. 9 shows (a) Dehydrated DEX film rehydrates upon addition of the PEG phase, (b) schematics of cell patterning due to rehydration of the DEX droplet and migration of cells into the gap, (c) experimental images of cell-excluded patterning and subsequent migration of MDA-MB-231 breast cancer cells.

The migration assay is based on movement of cells from a confluent monolayer into a circular cell-excluded area within the monolayer. To develop this assay, an aqueous two-phase system was utilized. A droplet of the denser aqueous phase, DEX, printed on a tissue culture dish is allowed to dehydrate and form a solid disk (FIG. 9a, left). Subsequent addition of the immersion PEG phase to the culture dish causes the dried DEX spot to rehydrate within a few minutes and form a droplet segregated from the surrounding PEG phase (FIG. 9a, right). Once the dried droplet starts rehydrating, an interfacial tension is generated between the aqueous PEG phase and the rehydrating aqueous DEX phase. This liquid-liquid interfacial tension is largest at the initial stages of the rehydration process due to the high concentration of the DEX polymer in the rehydrating droplet and decreases as the process continues toward equilibrium. When the PEG phase contains cells, the interfacial force at the boundary of PEG and DEX phases shields cells from crossing the interface between the two aqueous phases such that cells can only settle down around the droplet (FIG. 9b). Once cells adhere to the surface of the culture dish, the twophase media is washed out and replaced with regular media. This procedure generates a well defined circular cell-excluded area within a lawn of adhered cells and incubation results in the migration of cells and eventual closure of the available space (FIG. 9c).

Figure 10:
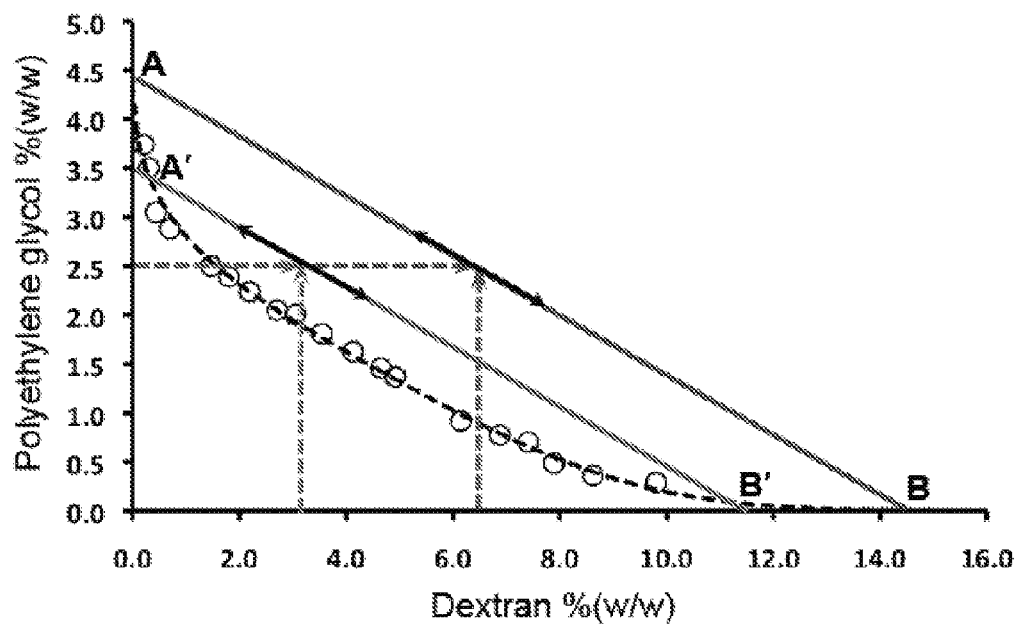
FIG. 10 shows a phase diagram of PEG35K-DEX500K and tie lines corresponding to 2.5% PEG-6.4% DEX (AB) and 2.5% PEG-3.2% DEX (A'B') two-phase systems.

The importance of interfacial tension for this cell patterning procedure was demonstrated by comparing the efficacy of two biphasic systems with a similar PEG concentration of 2.5% but different DEX concentrations of 3.2% and 6.4%. The interfacial tension of an ATPS is determined by the concentration of the phase forming polymers. A phase diagram of this polymer pair was used to determine the initial and final compositions of both systems (FIG. 10). The composition of the former ATPS (2.5% PEG-3.2% DEX) is closer to the critical point and thus the interfacial tension of this phase system is closer to its minimum, which corresponds to the critical point of the two-phase system. By increasing the DEX phase concentration to 6.4%, the phase system is removed farther from the critical point and the interfacial tension increases. Since the interfacial tension of an ATPS is directly proportional to the tie line length (Bamberger et al., *J. Colloid Interface Sci.* 1984, 99, 194), the length of the tlc lines (AB and A'B') for both ATPSs was measured as TLLAB=15.5 (% w/w) and TLLA'B'=11.5 (% w/w) and it was estimated that the ATPS with higher DEX concentration of 6.4% results in higher interfacial tension throughout the rehydration process with a ~26% increase in the interfacial tension in the fully hydrated state. From previous work of direct measurement of the interfacial tension of the 2.5% PEG-3.2% DEX ATPS (10 μJ/m2) (Tavana et al., *Adv. Mater.* 2010, 22, 2628) and the above tie line lengths, an interfacial tension of ~13 μJ/m2 is expected for the 2.5% PEG-6.4% DEX ATPS. A comparison of the patterns obtained with both phase systems confirms the influence of interfacial tension on pattern formation. Extreme sensitivity of partitioning properties of cells to changes in the interfacial tension of aqueous biphasic systems is consistent with our previous work that demonstrated a change of ~28% in the interfacial tension (10 μJ/m2 to 14 μJ/m2) significantly alters the fidelity of cellular patterns printed using ATPS microprinting technology (Tavana et al., supra). The principle defined above is general and may be utilized with other polymeric two-phase systems. As a general rule of thumb, cell printing and patterning with ATPSs is very sensitive to the interfacial tension, and thus phase-forming polymer concentrations. The concentration of polymers is optimally kept as low as possible to maintain the media cell-friendly and decrease the time required for cell adhesion, yet still generate an optimum force at the interface between the two phases to segregate cells.

Migration of MDA-MB-231 cells into the empty circular spot did not start until cells had completely spread and covered small intercellular spaces. Monitoring cells over time post printing showed that tight association of cells and the initiation of this process takes about 12 hrs. This is consistent with the finding that a threshold cell density is needed before the cellular gap closure process starts (Rosen et al., *Proc. Natl. Acad. Sci. USA* 1980, 77, 4760). At this point, cells present at the free edge experience pressure from the monolayer side. The presence of the circular cell-excluded discontinuity within the epithelium creates a net force on the boundary cells to move in the path of least resistance into the free available space until it is fully occupied by migrating cells (FIG. 1c). At the migrating front, cells spread out and formed fairly broad lamellipodial protrusions in the direction of migration (FIG. 11a) and showed clear staining for cortical actin filaments consistent with collective cell migration (FIG. 11b) (Poujade et al., *Proc. Natl. Acad. Sci. USA* 2007, 104, 15988). Formation of spikelike filopodia, which cells usually utilize as a mechanism to explore their microenvironment such as sensing chemical gradients (Kaur et al., *BMC Cell Biol.* 2008, 9, 61; Szczur et al., *Blood* 2006, 108, 4205) or expression of stress fibers that occur during individual migration of transformed cancer cells, were not observed (Micalizzi et al., *J. Mammary Gland Biol. Neoplasia* 2010, 15, 117).

High Throughput Cell Migration and Image Capture and Analysis

The cell migration technology was adapted to a high throughput format by printing a single DEX droplet in each well of a 96-microwell plate. Subsequent addition of cells suspended in the PEG phase generated parallel migration assays. A major challenge with the use of high-content cell migration platforms is image analysis and quantification of a large number of experiments. Cell migration was quantified by calculating the percentage of closure of the cell-excluded area over a given time period before the gap is completely closed, i.e. % Area closure=[(A1−A2)/A1]*100, where A1 and A2 denote the area of cell-excluded region at the beginning and endpoint of an experiment.

To determine A1 and A2, cells were stained with a fluorescent dye and imaged at a magnification of 2.8×. In order to perform unbiased measurements of area on a large number of images, an automatic protocol to process images and measure the void area within each image not occupied by migrating cells was developed. Using the scripting language of ImageJ (Abramoff et al., *Biophoton. Inter.* 2004, 11, 36), each image was loaded and its background was removed. Then all empty regions within the image were determined using thresholding. Subsequently, a set of despeckling, dilating and eroding steps was used to remove artifacts of thresholding and further correct the images by eliminating regions and objects that were too small compared to the size of a cell. This resulted in a single open area in the middle of the image with a precise contour of the edge formed by the migrating cells. To account for the small number of cells already inside this area, they were subtracted them from the total area. Overlaying the resulting image with the original unprocessed image confirms correct identification of the border of migrating cells and the accuracy of this image processing procedure. This procedure was performed automatically for all images resulting in the corresponding area data. After ensuring that the size of cell-excluded area was consistent throughout a plate for a given printed DEX droplet diameter, only cells at the end time point of the experiment to were stained and imaged, in order to save user time.

Dynamics of Cell Migration

Figure 11:
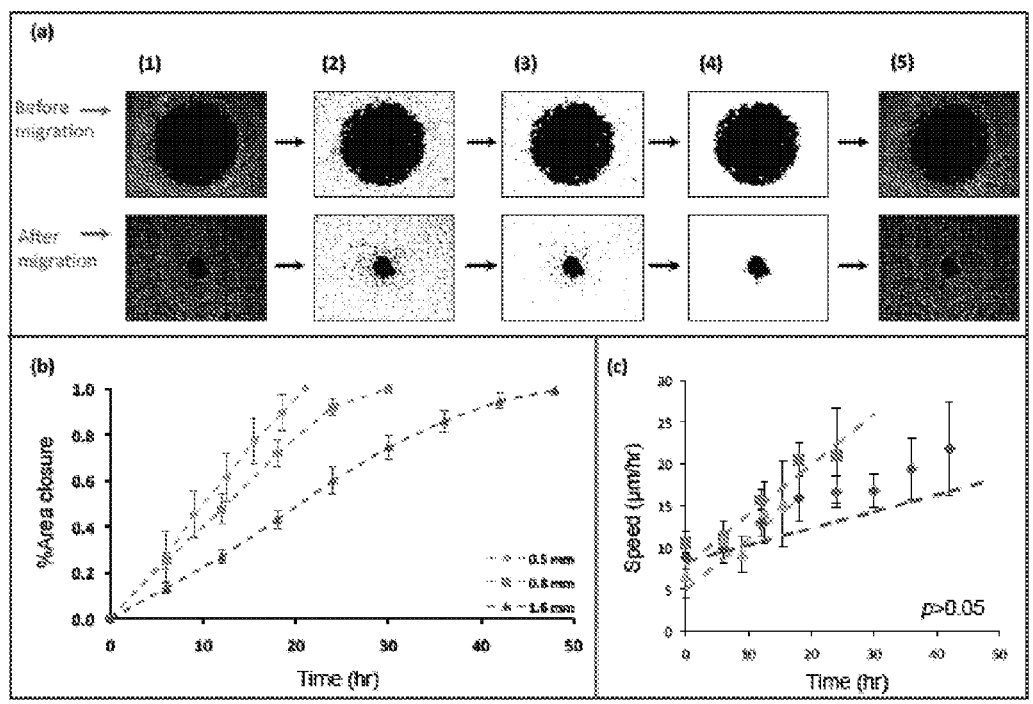
FIG. 11 shows (a) Sequence of image processing steps to determine the area of cell-excluded region in each well of a 96-well plate. Cells were stained with Calcein AM, (b) migration dynamics of MDA-MB-231 breast cancer cells into three different sizes of gap regions, (c) experimental and theoretical speed profiles of cells migrating into gap regions of different sizes.
Figure 14:
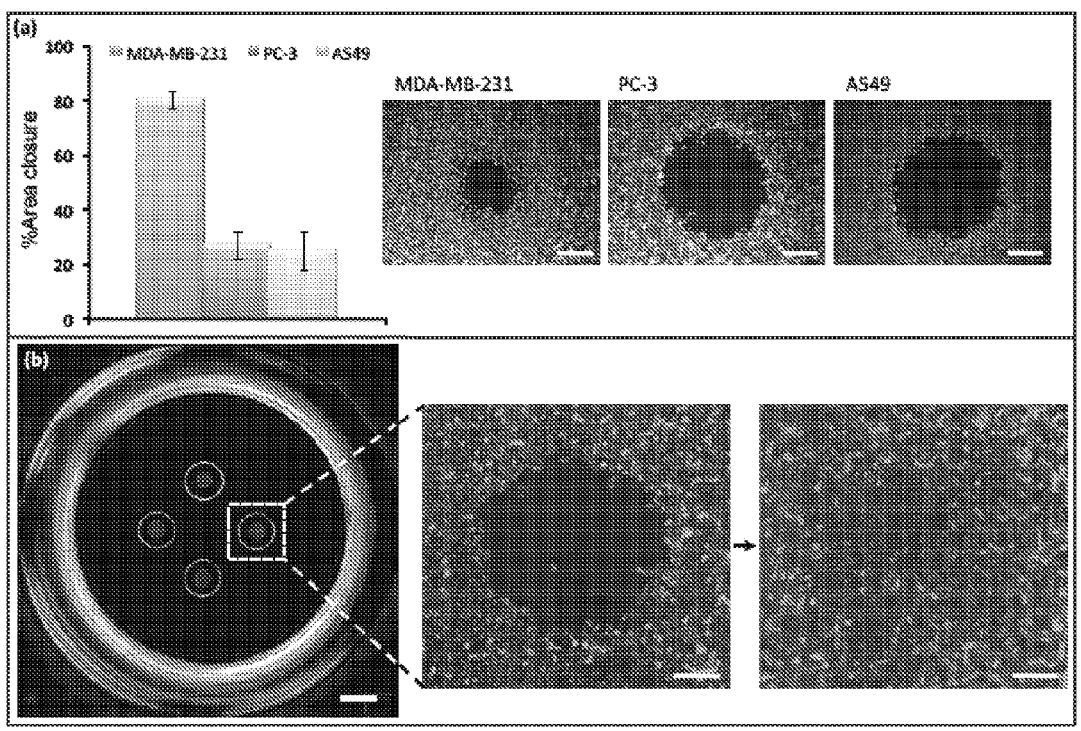
FIG. 14 shows (a) Comparison between migration of MDA-MB-231 breast cancer, A549 lung cancer, and PC-3 prostate cancer cells during similar experimental timeframe, (b) multiplexing cell-exclusion areas by printing four DEX droplets in each well of a 96-well plate and a representative image of cell migration into one of the four gaps.
Figure 15:
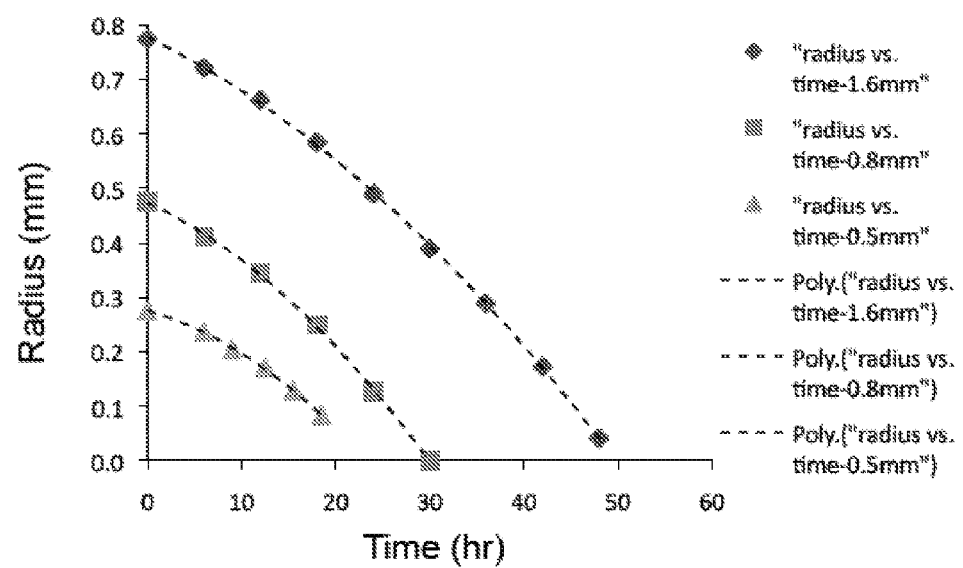
FIG. 15 show that the radius of the cell-excluded area decreases quadratically with time for gaps of different sizes.

Migration of MDA-MB-231 cells was studied in microwell plates containing cell-excluded spots with three different diameters of 1.6 mm, 0.8 mm, and 0.5 mm. Cell seeding density was adjusted to give equal number of cells per unit area, i.e. ~1400 cells/mm$^2$, in all three conditions. Imaging was carried out every 4-6 hrs until the initial gap was completely occupied by migrating cells. A gap size-dependent closure rate of cell-excluded areas was observed, with the highest rate of cell migration into the smallest gap and the slowest rate into the largest gap (FIG. 11b). Speed of cells was calculated as the average distance traversed by cells (e.g., change in radius) between each two imaging time points. It was found that the speed of cells continuously increases with time over the entire course of the migration process (FIG. 11c). Curve fitting to the approximated radius data was performed and it was found that radius decreases quadratically with time for all three cases. Differentiating the resulting equations gave theoretical speed relations as a function of time. Plotting these equations in FIG. 14c shows that the experimental data follow the theoretical curves and overall, cells accelerate more in the cases with smaller gap sizes (0.5 and 0.8 mm). It was not possible to distinguish between acceleration of cells in these three cases within experimental error. Acceleration of cells with the closure time is consistent with previous reports (Poujade et al., supra; Rosen et al., supra).

Effect of Blebbestatin on Cell Migration

Figure 12:
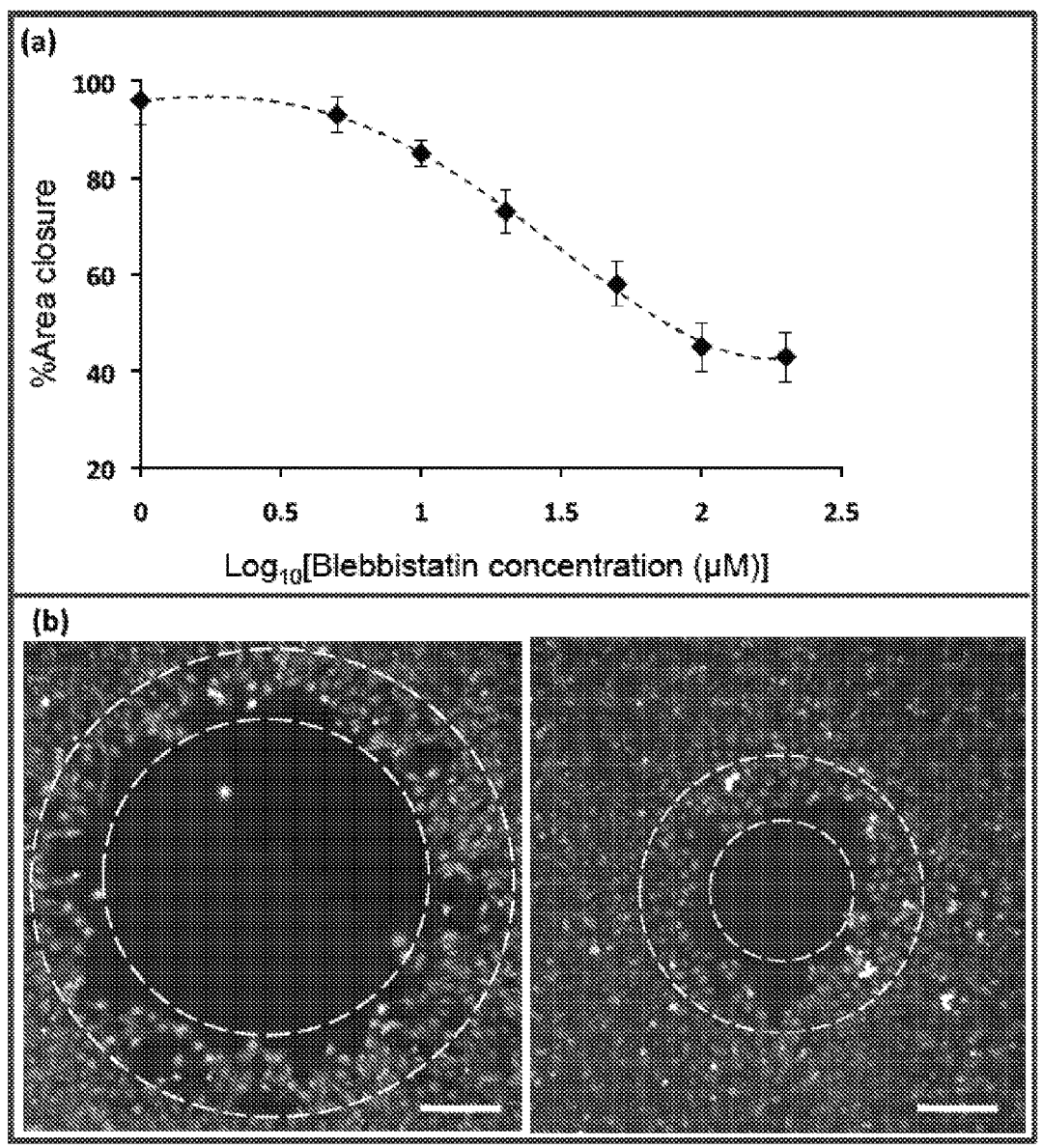
FIG. 12 shows (a) Blebbistatin shows dose-dependent inhibition of motility of MDA-MB-231 breast cancer cells. (b) cells at the migrating front, between two dashed circles, dissociated and elongated after treatment with blebbistatin (left panel) compared to the control condition of no blebbistatin treatment (right panel).

The present invention is not limited to a particular mechanism. Indeed, an understanding of the mechanism is not necessary to practice the present invention. Nonetheless, the basic mechanism of cell motility is similar in many cases and involves polarization of cell body accompanied by continuous reorganization of actin cytoskeleton, integrin-mediated adhesion to the underlying substrate, formation of membrane protrusions at the cell front, traction of cell body through actomyosin-mediated contraction, and disassembly of adhesion sites at the rear of the cell to enable the cell translocate. As a test of the platform to assess cell migration, cells were treated with a potent inhibitor of machinery of cellular motility, blebbistatin. This compound interferes with rigid actomyosin cross-bridging and abates cell motility (Kovacs et al., *J. Biol. Chem.* 2004, 279, 35557; Watanabe et al., *Am. J. Physiol. Cell Physiol.* 2010, 298, C1118). MDA-MB-231 cells were treated with six different concentrations of blebbistatin ranging from 5-200 μM for 18 hrs. Cells showed a dose-dependent response to blebbistatin and their migration capacity decreased significantly with increasing concentration of the inhibitor, especially at concentrations greater than 50 μM (FIG. 12a). With the experimental conditions, the data indicate an IC50 value of 31.8 μM (BioDataFit software). It was also observed that cells at the free edge became more elongated and lost close associations after blebbistatin treatment (FIG. 12b), similar to previous reports (Petroll et al., *J. Cell Physiol.* 2008, 217, 162). This set of experiments confirms that the biphasic cell-exclusion patterning provides a reliable cell migration platform for testing effects of compounds targeting cell motility. Statistical analysis was performed to assess the quality of the migration assay and a value of 0.62 for the Z' factor was obtained using data from 200 μM blebbistatin test as the positive control and no blebbistatin treatment as the negative control (Zhang et al., *J. Biomol. Scr.* 1999, 4, 67). This value indicates the high quality and robustness of the cell-exclusion migration assay. The Z' factor is a measure of the robustness of high throughput screens where values in the range of 0.5-1.0 are regarded as excellent assays (Zhang et al., supra).

Screening Multiple Inhibitors of Cell Migration

Figure 13:
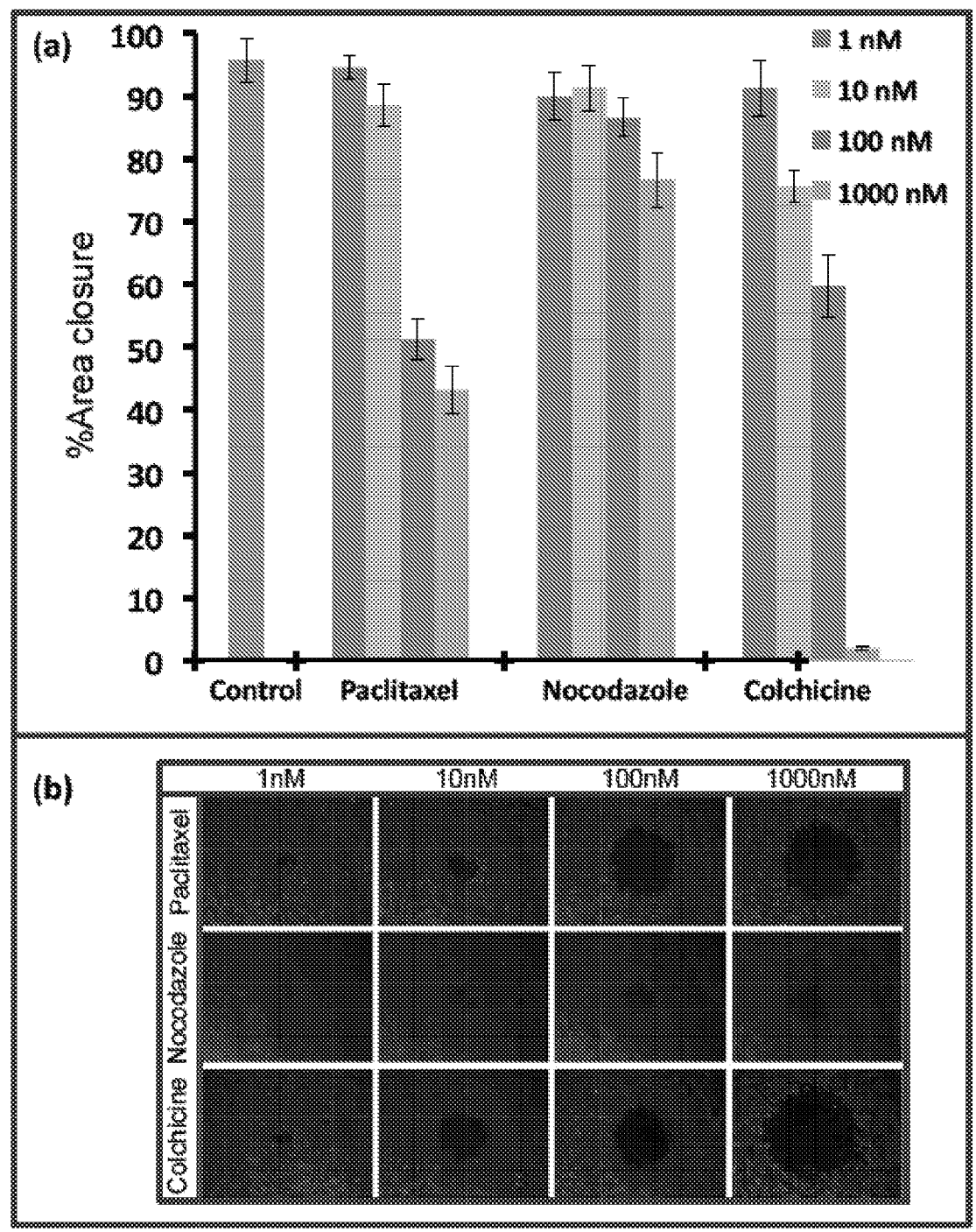
FIG. 13 shows (a) The effect of three different drugs, paclitaxel, nocodazole, and colchicine, on the migration of MDA-MB-231 breast cancer cells, (b) experimental images of cells treated with four different concentrations of each compound.

The effect of three different compounds on migration of MDAMB-231 cells was screened. Paclitaxel, colchicine, and nocodazole, each of which interferes with cell proliferation and normal dynamic function of microtubules were utilized. Paclitaxel is a potent cancer chemotherapeutic agent that stabilizes microtubules and prevents their depolymerization to tubulin monomers (Schiff et al., *Proc. Natl. Acad. Sci. USA* 1980, 77, 1561; Yvon et al., *Mol. Biol. Cell* 1999, 10, 947). Colchicine and nocodazole, on the other hand, inhibit polymerization of tubulin monomers to microtubules (Cronstein et al., *Clin. Invest.* 1995, 96, 994; Mythreye et al., *Proc. Natl. Acad. Sci. USA* 2009, 106, 8221). Drugs were tested at four different orders of magnitude of concentration in the range of 1-1000 nM. Cells were treated with compounds for a 2 hr period because it has been indicated that these agents can be effective even at short treatment times. Paclitaxel showed potency for inhibiting cell motility within the concentration range of 10-100 nM (FIG. 13*a*, 13*b*—top row), whereas colchicine reduced cell motility in a dose-dependent manner (Tran et al., *Biochem. Biophys. Res. Comm.* 2009, 379, 304), especially above 100 nM (FIG. 13*a*, 16*b* bottom row). Nocodazole was the least potent among these three drugs and reduced migration by less than 20% only (FIG. 13*a*, 13*b*-middle row). This test demonstrates the suitability of the platform for high throughput simultaneous screening of multiple drug candidates to identify most potent agents in inhibiting cell migration for different dosages and treatment times.

Versatility and Flexibility of the Method

To demonstrate generality of the method for use with different cell types, two other cancer cell lines were tested in addition to the breast cancer cells (MDA-MB-231): A549 lung cancer cells and PC3 prostate cancer cells. The results in FIG. 14*a* show that within 30 hrs of incubation, 231 cells migrate much faster than the other two cell lines and occupy 80% of the available space. Both A549 and PC-3 cells showed similar reduced migratory behavior closing about 25% of the cell-excluded gap within this timeframe. Although the incubation time needs to be adjusted to allow completion of migration of the slower moving cells, this experiment demonstrates the broad applicability of the method to multiple cell types. In addition, it demonstrates the capability of increasing the throughput of experiments by creating four cell excluded regions within a single well of a 96-array format microwell (FIG. 14*b*). Such multiple cell-exclusion patterning enhances statistical confidence of assays. It also demonstrates the flexibility and versatility of the rehydration-mediated cell exclusion patterning procedure.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in electrical engineering, optics, physics, and molecular biology or related fields are intended to be within the scope of the following claims.

We claim:
1. A system, comprising:
   a) a dextran (DEX) solution, wherein said DEX solution is dehydrated on a solid or semi-solid support;
   b) a polyethylene glycol (PEG) solution comprising cells, wherein said PEG solution is not dehydrated, wherein said PEG solution is less dense than said DEX solution, and wherein said PEG solution rehydrates said DEX solution to form an aqueous two-phase system when mixed, wherein said DEX and PEG are present in the aqueous two-phase system at a concentration above the binodal curve concentration for aqueous two phase system formation, and wherein said cells are excluded from said DEX solution by the interfacial force at the boundary between said DEX and PEG in said aqueous two phase system; and
   c) said solid or semi-solid support.

2. The system of claim 1, wherein said system further comprises reagents for performing an assay.

3. The system of claim 2, wherein said assay is an immunoassay or a nucleic acid detection assay.

4. The system of claim 1, wherein said PEG is present at a concentration greater than 0.5%.

5. The system of claim 1, wherein said DEX is present at a concentration greater than 1.0%.

6. A method, comprising
   contacting a portion of a solid or semi-solid support with a PEG solution comprising cells, said solid or semi-solid support comprising dehydrated DEX, wherein said DEX is denser than said PEG, wherein said PEG solution rehydrates said dehydrated DEX solution and said DEX and PEG solutions form an aqueous two-phase system when mixed, wherein said DEX and PEG are present in the aqueous two-phase system at a concentration above the binodal curve concentration for aqueous two phase system formation, and wherein said cells are excluded from said DEX solution by the interfacial force at the boundary between said DEX and PEG in said aqueous two phase system.

7. The method of claim 6, wherein said cells form patterns in multi well plates.

8. The method of claim 7, wherein said cells are used in an assay.

9. The method of claim 8, wherein said assay is a cell migration assay.

10. A method, comprising
   a) arraying a plurality of first solutions comprising i) a DEX solution; and ii) reagents for performing an assay on a solid or semi-solid support;
   b) dehydrating said DEX solution to form dehydrated spots on said support;
   c) contacting said dehydrated spots with a PEG solution comprising cells, wherein said PEG solution is less dense than said DEX, wherein said PEG solution rehydrates said DEX solution to form an aqueous two-phase system, and wherein said DEX and PEG are present in the aqueous two-phase system at a concentration above the binodal curve concentration for aqueous two phase system formation, and wherein said cells are excluded from said DEX solution by the interfacial force at the boundary between said DEX and PEG in said aqueous two phase system solution.

\* \* \* \* \*